United States Patent [19]

Kodera et al.

[11] 4,427,772
[45] Jan. 24, 1984

[54] APPARATUS HAVING AUTOMATIC CALIBRATION FOR DETERMINING HYDROGEN PEROXIDE CONCENTRATION

[75] Inventors: Yasuo Kodera, Shiki; Toshiaki Ishii, Niiza; Minoru Ohashi, Oizumi, all of Japan

[73] Assignee: Oriental Yeast Co. Ltd., Tokyo, Japan

[21] Appl. No.: 290,574

[22] Filed: Aug. 6, 1981

[30] Foreign Application Priority Data

Sep. 18, 1980 [JP] Japan .................. 55-128558

[51] Int. Cl.³ .................. G01N 27/30; G01N 31/10; G01N 35/00
[52] U.S. Cl. .................. 435/27; 204/403; 435/28; 435/291
[58] Field of Search .................. 435/27, 28, 291; 204/195 R, 195 F, 195 B, 1 T

[56] References Cited

U.S. PATENT DOCUMENTS 3,838,034  9/1974  Groves .................. 435/291 X

FOREIGN PATENT DOCUMENTS 1199565  7/1970  United Kingdom .................. 435/807

*Primary Examiner*—Sidney Marantz
*Attorney, Agent, or Firm*—Parkhurst & Oliff

[57] ABSTRACT

Apparatus for determining a concentration of hydrogen peroxide in an aqueous solution featuring (A) a sampling system, (B) a reaction system, (C) an oxygen concentration determining system, (D) an automatic calibration system and (E) a sequence circuit system. One cycle of determination consists of three operating stages. In the first stage, a zero point adjustment and a span adjustment are established to properly calibrate the sensitivity of an oxygen detector, air saturated water or a fresh sample being used as the standard. In the second stage, a sample is introduced and hydrogen peroxide in the sample is decomposed with a hydrogen peroxide decomposing agent. The concentration of oxygen dissolved in the sample is then determined by means of the oxygen detector. In the third stage, the reaction vessel is washed with fresh water or a fresh sample after the discharging of the used sample. Determinations are repeated at a predetermined time interval under the control of the sequence circuit system. Preferably, an oxygen probe is used as the oxygen detector and a catalase solution is used as the hydrogen peroxide decomposing agent.

11 Claims, 5 Drawing Figures

APPARATUS HAVING AUTOMATIC CALIBRATION FOR DETERMINING HYDROGEN PEROXIDE CONCENTRATION

BACKGROUND OF THE INVENTION

1. Field of the Invention

The present invention relates to an apparatus for determining the concentration of hydrogen peroxide in a liquid and more particularly relates to a new apparatus for automatically determining concentrations of hydrogen peroxide at certain time intervals in a repeated manner under a sequence control.

2. Description of the Prior Art

As is well known, hydrogen peroxide has a strong oxidizing action and is widely used for sterilizing, bleaching and the like, and in various other applications, such as for instance, foodstuffs, such as noodles and boiled fish paste products etc., fiber, pulp, detergent, cosmetics and the like. Accordingly, hydrogen peroxide is subjected to strict legal regulations particularly with respect to its residual quantities in foodstuffs, waste water and the like.

Thus, when hydrogen peroxide is used in an application such as those mentioned above, it is necessary to quickly determine the concentration of hydrogen peroxide in every step of manufacturing or processing.

Further, it is very important to control the concentration of hydrogen peroxide so that the optimum oxidation, bleaching, sterilization and the like may be effected. However, no apparatus has been heretofore proposed which can automatically and exactly determines the concentration of hydrogen peroxide.

SUMMARY OF THE INVENTION

The present invention provides an apparatus by which a concentration of hydrogen peroxide is automatically and continuously determined with excellent accuracy over a long period of time.

The apparatus for determining a concentration of hydrogen peroxide in accordance with the present invention essentially comprises:

(A) a sampling system in which a certain quantity of hydrogen peroxide aqueous solution is sampled;

(B) a reaction system in which the sample is decomposed with a hydrogen peroxide decomposing agent;

(C) an oxygen concentration determining system in which the quantity of oxygen dissolved in the sample is determined as an electric current;

(D) an automatic calibration system which maintains the sensitivity of an oxygen detector; and (E) a sequence circuit system for controlling the operation of the respective systems described above.

An oxygen probe is preferably used as the oxygen detector in the reaction system.

An aqueous catalase solution is preferably used as the hydrogen peroxide decomposing agent in the reaction system.

One cycle of determination in the present invention consists of three stages. Specifically, the first stage comprises the steps of introducing water or a fresh sample into a reaction vessel, subjecting the water to aeration, making a zero point adjustment and a span adjustment in the automatic calibration system to calibrate the sensitivity of the oxygen detector and then discharging the water. The second stage comprises the steps of introducing a certain quantity of sample into the reaction vessel, subjecting the sample to aeration, adding a hydrogen peroxide decomposing agent to the sample, determining the concentration of oxygen dissolved in the sample by means of the oxygen detector, holding the determined value and then discharging the used sample. The third stage comprises the step of washing the reaction vessel with fresh water or a fresh sample. The individual determination cycle comprising the three stages described above is repeated at a certain time interval under a sequence control.

Thus it is an object of the present invention to provide a new apparatus for determining the concentration of hydrogen peroxide which ensures automatic and exact determinations over a long period of time without the necessity for replacement of the oxygen detector with a new one.

It is another object of the present invention to provide an apparatus for determining the concentration of hydrogen peroxide which ensures exact determinations with any sample having a relatively low concentration of hydrogen peroxide in the range of 0.5 to 10 ppm.

Other objects of the present invention will be ovbious from the following description with reference to the accompanying drawings.

BRIEF DESCRIPTION OF THE ACCOMPANYING DRAWINGS

FIG. 1 schematically illustrates an apparatus for determining the concentration of hydrogen peroxide in an aqueous solution in accordance with an embodiment of the present invention.

DETAILED DESCRIPTION OF THE PREFERRED EMBODIMENT OF THE INVENTION

Figure 1:
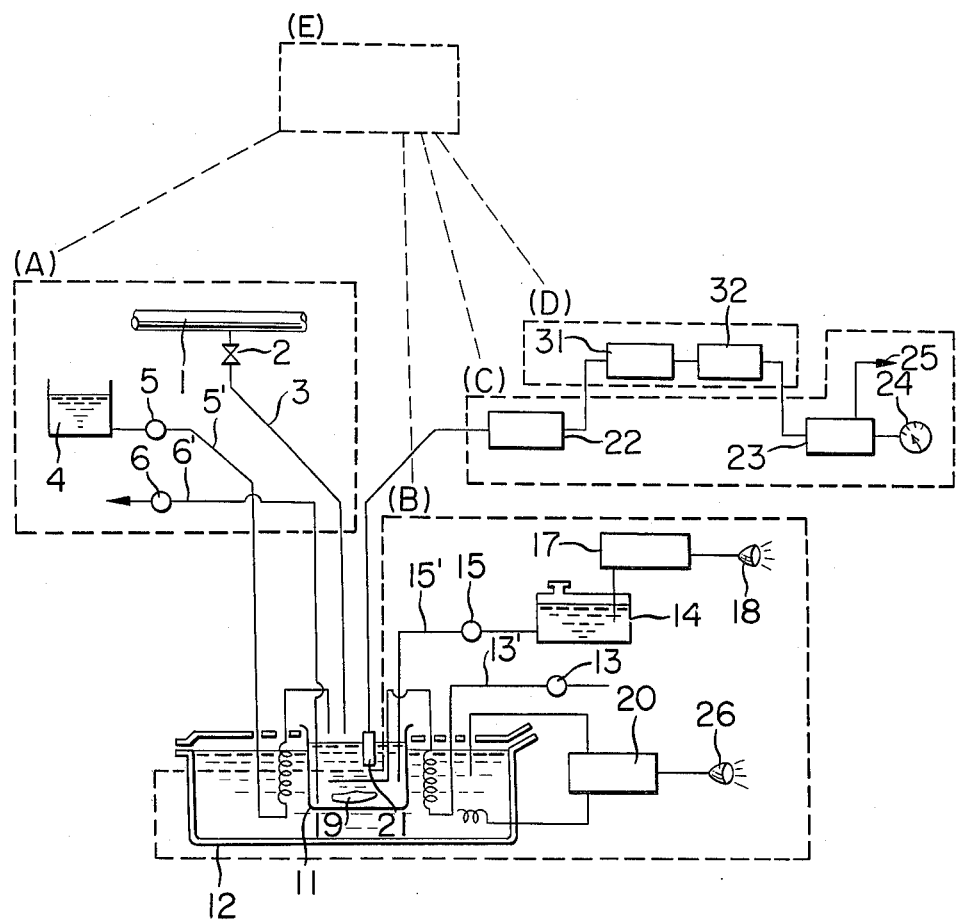

Now the present invention will be described in more detail with reference to the accompanying drawings. Basically, the apparatus in accordance with the present invention comprises (A) a sampling system, (B) a reacting system, (C) an oxygen concentration determining system, (D) an automatic calibration system, and (E) a sequence circuit system, wherein the last mentioned system serves to control the operation of said systems (A), (B), (C) and (D). The structure and function of the respective systems are be individually described below.

First, the sampling system (A) comprises a sample transporting pipe 1, a solenoid valve 2, a sample delivery pipe 3, a water tank 4, a water supply pump 5, a water supply pipe 5', a water discharge pump 6 and a water discharge pipe 6'.

Second, the reacting system (B) comprises a reaction vessel 11, a constant temperature controlled water bath 12, a pneumatic pump 13, an air supply pipe 13', a catalase tank 14, a catalase supply pump 15, a catalase supply pipe 15', a level detecting circuit 17, an alarm circuit 18, a stirrer 19 and a control circuit 20 for controlling the temperature of the constant temperature controlled water bath.

Third, the oxygen concentration determining system (C) comprises an oxygen probe 21, a preamplifier 22, a hold circuit 23, an indicator 24 and a transmission output terminal 25.

Fourth, the automatic calibration system (D) comprises an automatic calibration circuit 31 and an oxygen probe sensibility degradation alarm circuit 32.

The operation of the respective systems described above is controlled by (E) the sequence circuit system.

When the water supply pump 5 starts operation, water in the water tank 4 or a fresh sample is introduced through the water supply pipe 5' into the reaction vessel 11 in which the stirrer 19 is rotated. It should be noted that the reaction vessel 11 is immersed in the constant temperature controlled water bath 12 which is equipped with a water tank 4, a water supply pump 5, a water supply pipe 5', a water discharge pump 6 and a water discharge pipe 6'.

The constant temperature controlled water bath 12 is equipped with the constant water temperature control circuit 20 which is provided to detect the volume of the water and control the temperature of the water, whereby the optimum reaction temperature is ensured at all times. Also provided is an alarm circuit 26.

When the pneumatic pump 13 starts its operation, air is blown into the water in the reaction vessel 11 through the air supply pipe 13' so that aeration of the water takes place until the water in the reaction vessel 11 becomes saturated with air.

Next, the sensitivity of the oxygen probe 21 connected to the preamplifier 22 is calibrated by determining the amount of oxygen dissolved in the air saturated water or sample.

Heretofore, the oxygen probe has normally been caibrated by using a separate standard aqueous solution of hydrogen peroxide. However, it has been found that an aqueous solution of hydrogen peroxide is not preferable as a standard, because hydrogen peroxide is very unstable. In view of the disadvantages of the conventional methods of calibration. The automatic calibration system in the apparatus of the present invention is constructed such that the automatic calibration circuit 31 is operated by using air saturated water or sample as a standard in place of a separate aqueous solution of hydrogen peroxide.

In the present invention, a zero point adjustment and a span adjustment of hydrogen peroxide indicator are carried out from the output of the oxygen probe 21 which is obtained by determining the amount of oxygen dissolved in the air saturated water or sample.

An output of the oxygen probe can be used to calculate the hydrogen peroxide concentration.

For instance, pure water saturated with air at a temperature of 30° C. contains 7.53 ppm oxygen dissolved therein which corresponds to a hydrogen peroxide concentration of about 7 ppm.

Thus, the calibrating circuit in the apparatus of the present invention is designed in such a manner as to indicate the existing concentration of hydrogen peroxide in ppm.

It should be noted that the automatic calibration circuit 31 performs two functions, one of them being to correct and keep constant the sensitivity of the oxygen probe 11 and the other one being to issue an alarm when the oxygen probe 11 fails to keep its output constant due to an excessive decrease in its sensitivity.

Figure 3:
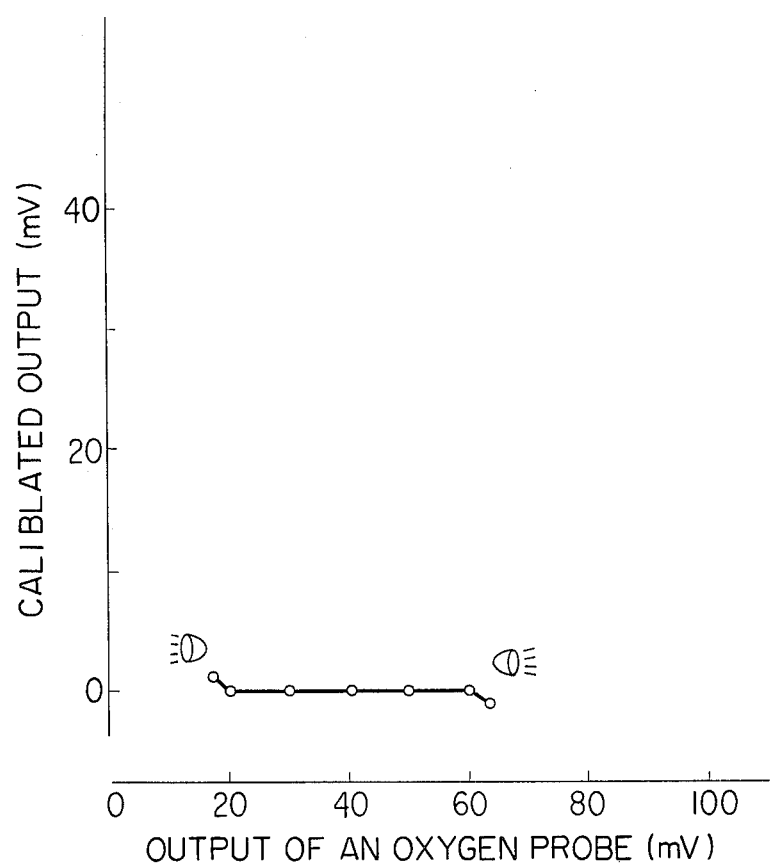
FIG. 3 illustrates a zero point adjustment of the present apparatus.
Figure 4:
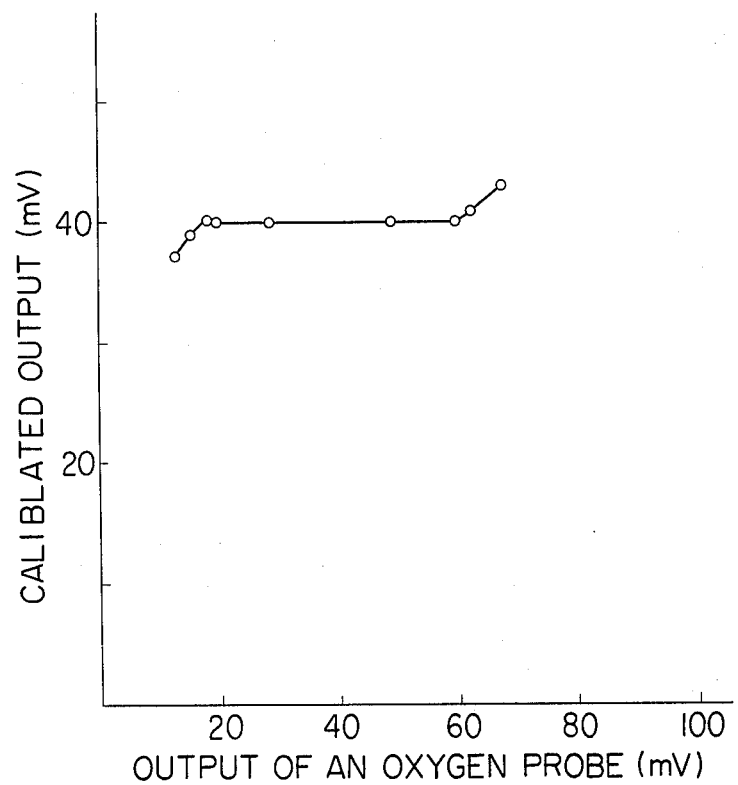
FIG. 4 illustrates a span adjustment of the present apparatus. The mean value of oxygen probe output being 40 mV.
Figure 5:
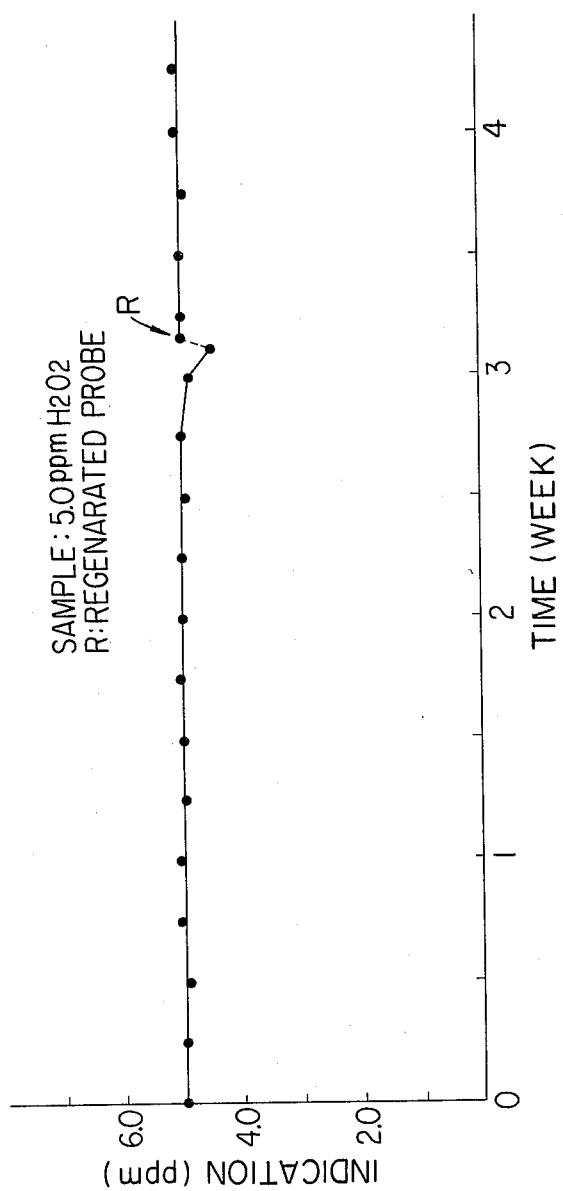
FIG. 5 shows an example of continuous determination of the $H_2O_2$ concentrations using the present apparatus.

Further, it should be noted that an automatic calibration circuit with servomotor incorporated therein ensures the required zero point and span adjustments and keeps the output of the oxygen probe 11 constant, as long as the sensitivity of the oxygen probe does not increase or decrease more than 50% (See FIG. 3 and FIG. 4). Thus, this calibration circuit makes it possible to continuously operate the apparatus for a considerably long period of time (one week to one month) without any necessity for replacing the oxygen probe with a new one (See FIG. 5).

After completion of the calibration of the oxygen probe 11, water in the reaction vessel 11 is discharged to the outside via the pipe 6' by means of the discharge pump 6.

A certain quantity of sample is taken from the sample supply pipe 3 by operating the solenoid valve 2 and then is put into the reaction vessel 11 via the pipe 3. By operating the pneumatic pump 13 again, air is blown into the sample via the pipe 13' and the sample thereby becomes saturated with air by way of aeration.

After completion of aeration, the catalase pump 15 starts its operation and thereby a certain quantity of catalase solution is taken from the catalase tank 14 and is introduced into the reaction vessel 11 via the pipe 15'. The sample is subjected to a slow and steady stirring caused by the stirrer 19, whereby hydrogen peroxide decomposition takes place with the aid of the enzyme catalase.

The increased quantity of dissolved oxygen due to the aforesaid oxygen reaction is determined by means of the oxygen probe 11, the determined current is amplified by the preamplifier 22, its determined value is retained with the aid of a holding circuit 23 until a next determined value is obtained, and thereafter it is indicated on an indicator 24.

After completion of the determination, the sample is discharged out of the apparatus via the pipe 6' by operating the discharge pump 6.

When the water supply pump 5 starts its operation and water in the tank 4 or a fresh sample is introduced into the reaction vessel 11, the latter is washed with water in cooperation with the pump and stirrer. After completion of washing, the wash water is discharged out of the apparatus. After completely washing the reaction vessel 11, one cycle of operations is over. Here, it should be noted that during the above cycle, all the operations are controlled by a sequence circuit system, and that after the completion of one cycle the cycle is then repeated.

Thus, the apparatus in accordance with the present invention makes it possible to automatically and exactly determine a concentration of hydrogen peroxide at certain short intervals for a long period of time.

The sensitivity of the oxygen detector becomes degraded as operations proceed, but in order to compensate for this degradation the apparatus of the present invention is provided with an automatic calibration circuit with a servomotor incorporated therein which allows the oxygen detector to be automatically corrected when its sensitivity decreases to some extent, whereby it is ensured that the oxygen detector keeps its output substantially constant. Thus it is possible to determine exactly a concentration of hydrogen peroxide for over a long period of time (one week to one month) without any necessity for replacement of the oxygen detector.

Further, since the apparatus in accordance with the present invention is operated with the use of stable air saturated water as a standard, a zero adjustment and a span adjustment are very consistently carried out.

Furthermore, since calibration is automatically effected each time determinations are carried out, the precision of the determination values obtained can be maintained at a high level over a long period of time.

Figure 2:
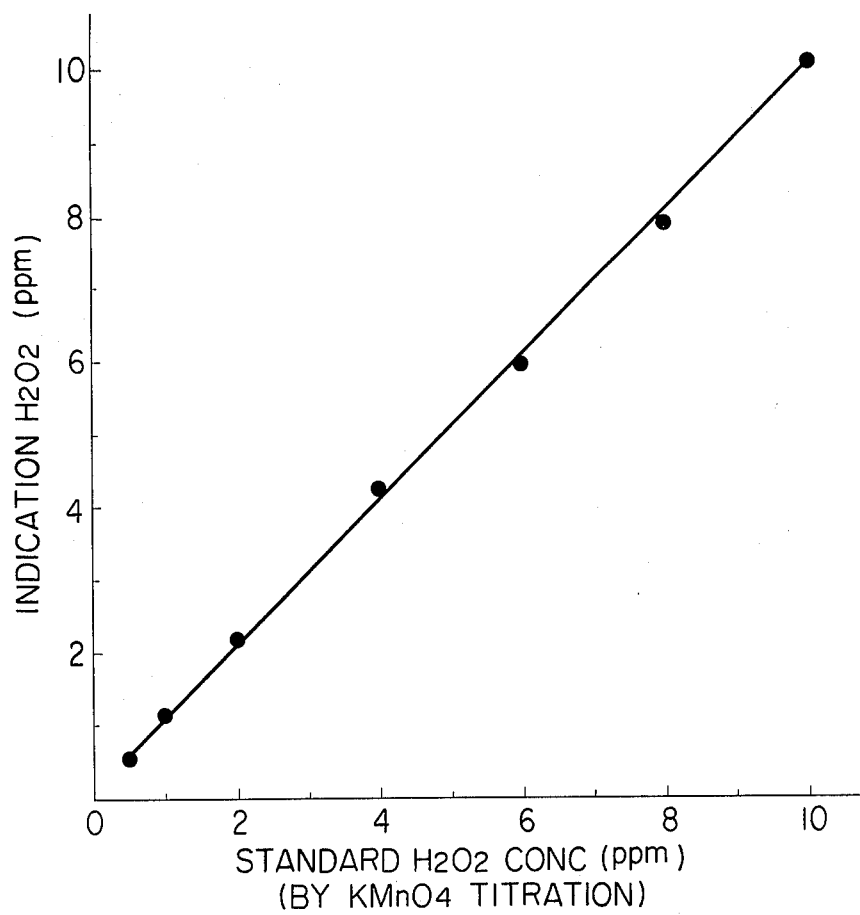
FIG. 2 is a calibration curve of $H_2O_2$ when using the present apparatus.

The apparatus in accordance with the present invention has as an additional advantage the fact that lower concentrations of hydrogen peroxide, in the range of 0.5 to 10 ppm for instance, can be exactly determined (see FIG. 2).

Finally, it should be noted that the apparatus in accordance with the present invention makes it possible to automatically control a concentration of hydrogen peroxide in an aqueous solution to be inspected.

What is claimed is:

1. An apparatus for determining a concentration of hydrogen peroxide in an aqueous solution comprising:
   (A) sample means for sampling a certain quantity of aqueous hydrogen peroxide solution;
   (B) reacting means for decomposing the sample with a hydrogen peroxide decomposing agent;
   (C) oxygen concentration determining means for determining the quantity of oxygen dissolved in the sample as an electric current, said dissolved oxygen being generated during the decomposition;
   (D) automatic calibration means for keeping constant the sensitivity of an oxygen detector which calibration means comprises means for introducing a quantity of liquid into a reaction vessel, means for aerating the liquid, and means for using the aerated liquid as a standard to calibrate the sensitivity of the concentration determining means; and
   (E) sequence circuit means for controlling the operation of the respective means described above.

2. An apparatus as set forth in claim 1, wherein said hydrogen peroxide decomposing agent is an aqueous catalase solution.

3. An apparatus as set forth in claim 1, wherein said sampling means (A) comprises a sample transporting pipe, a sample delivery pipe connected to said sample transacting pipe to deliver a certain quantity of sample, a solenoid valve located in position in said sample delivery pipe, a water tank, a water supply pump, a water supply pipe, a water discharge pump and a water discharge pipe.

4. An apparatus as set forth in claim 1, wherein said reaction means (B) comprises a reaction vessel, a constant temperature controlled water bath, a pneumatic pump, an air supply pipe, a hydrogen peroxide decomposing agent tank, a hydrogen peroxide decomposing agent supply pump, a hydrogen peroxide decomposing agent supply pipe, a hydrogen peroxide decomposing agent level detecting circuit, an alarm circuit connected to said level detecting circuit, a stirrer disposed in the bottom of said reaction vessel and a control circuit for controlling water temperature and volume in said constant temperature controlled water bath.

5. An apparatus as set forth in claim 1, wherein said oxygen concentration determining means (C) comprises an oxygen detector immersed in the reaction vessel, a preamplifier, a hold circuit, an indicator and an output transmission terminal.

6. An apparatus as set forth in claim 1, wherein said automatic calibration means (D) further comprises an automatic calibration circuit connected to a preamplifier in the oxygen concentration determining means and an oxygen detector sensitivity degradation alarm circuit.

7. A method for determining a concentration of hydrogen peroxide in an aqueous solution, comprising:
   (a) a first stage comprising the steps of introducing a certain quantity of a liquid into a reaction vessel, subjecting the liquid to aeration, using the aerated liquid as a standard for calibration, calibrating the sensitivity of an oxygen concentration determining means by making a zero point adjustment and a span adjustment in an automatic calibration means, and discharging the aerated liquid from the reaction vessel;
   (b) a second stage comprising introducing a certain quantity of a test sample into a reaction vessel, subjecting the test sample to aeration, adding a certain quantity of a hydrogen peroxide decomposing agent to the test sample, decomposing the hydrogen peroxide present in the test sample to water and oxygen dissolved in the test sample by means of the hydrogen peroxide decomposing agent, determining the concentration of the oxygen dissolved in the test sample by means of the oxygen concentration determining means, holding the determined value, and discharging the used test sample; and
   (c) a third stage comprising washing the reaction vessel with a liquid, so that each individual hydrogen peroxide concentration determination comprises said first, second and third stages, said stages being repeated at a certain time interval under a sequence control.

8. The method of claim 7, wherein the liquid introduced into the reaction vessel in said first stage and the liquid used to wash the reaction vessel in said third stage is water.

9. The method of claim 7, wherein the liquid introduced into the reaction vessel in said first stage and the liquid used to wash the reaction vessel in said third stage is a fresh test sample.

10. The method of claim 7, wherein the liquid introduced into the reaction vessel in said first stage is water and the liquid used to wash the reaction vessel in said third stage is a fresh test sample.

11. The method of claim 7, wherein the liquid introduced into the reaction vessel in said first stage is a fresh test sample and the liquid used to wash the reaction vessel in said third stage is water.

* * * * *